(12) United States Patent
Feng et al.

(10) Patent No.: US 10,340,039 B2
(45) Date of Patent: Jul. 2, 2019

(54) MANAGING PATIENT DEVICES BASED ON SENSOR DATA

(71) Applicant: HITACHI, LTD., Tokyo (JP)

(72) Inventors: Shuang Feng, Milpitas, CA (US); Abhay Mehta, Austin, TX (US); Hsiu-Khuern Tang, San Jose, CA (US); Hiroaki Ozaki, Mountain View, CA (US); Haiyan Wang, Fremont, CA (US); Song Wang, San Carlos, CA (US)

(73) Assignee: Hitachi, Ltd., Tokyo (JP)

( * ) Notice: Subject to any disclaimer, the term of this patent is extended or adjusted under 35 U.S.C. 154(b) by 488 days.

(21) Appl. No.: 15/246,668

(22) Filed: Aug. 25, 2016

(65) Prior Publication Data
US 2018/0060492 A1    Mar. 1, 2018

(51) Int. Cl.
| | | |
|---|---|---|
| *G06F 15/16* | (2006.01) | |
| *G16H 10/60* | (2018.01) | |
| *G06F 16/28* | (2019.01) | |
| *G06F 16/22* | (2019.01) | |
| *G16H 40/63* | (2018.01) | |
| *G16H 40/20* | (2018.01) | |
| *G16H 50/70* | (2018.01) | |

(52) U.S. Cl.
CPC ......... *G16H 10/60* (2018.01); *G06F 16/2237* (2019.01); *G06F 16/285* (2019.01); *G16H 40/20* (2018.01); *G16H 40/63* (2018.01); *G16H 50/70* (2018.01)

(58) Field of Classification Search
CPC .... G16H 10/60; G16H 50/70; G06F 16/2237; G06F 16/285

USPC ............................................. 709/206; 705/2
See application file for complete search history.

(56) References Cited

U.S. PATENT DOCUMENTS

| | | | | |
|---|---|---|---|---|
| 5,781,442 A | * | 7/1998 | Engleson | G16H 40/20 700/214 |
| 6,801,802 B2 | | 10/2004 | Sitzman et al. | |
| 9,119,598 B2 | | 9/2015 | Engelbrecht et al. | |
| 2003/0009244 A1 | * | 1/2003 | Engleson | G06Q 50/22 700/86 |
| 2004/0172302 A1 | * | 9/2004 | Martucci | A61B 5/0002 705/2 |

(Continued)

FOREIGN PATENT DOCUMENTS

EP  3287918 A1 * 2/2018 ............. G16H 10/60

*Primary Examiner* — Hee Soo Kim
(74) *Attorney, Agent, or Firm* — Mattingly & Malur, PC

(57) ABSTRACT

In some examples, a computing device may receive sensor data associated with a plurality of patient devices that are associated with a plurality of patients. The computing device may further receive caregiver records corresponding at least partially to the sensor data. At least two groups of indicators may be determined from the caregiver records, such a based on a selected subject. Further, the computing device may determine a plurality of clusters from the sensor data. Based on the plurality of clusters and the at least two groups, the computing device may determine an indication of a discrepancy in care for a patient of the plurality of patients. Based on the indication of the discrepancy, the computing device may send at least one of a notification to a caregiver computing device, a notification to a monitoring computing device, or a control signal to one of the patient devices.

20 Claims, 7 Drawing Sheets

(56) References Cited

U.S. PATENT DOCUMENTS

2008/0306357 A1 12/2008 Korman
2010/0249541 A1 9/2010 Geva et al.
2016/0092721 A1* 3/2016 Kanagasingam ..... G06T 7/0012
                                                          348/14.08

* cited by examiner

702

| Distance | Cluster | |
|---|---|---|
| | A | B |
| Group a | 1.5 | 3 |
| Group b | 0.4 | 5 |

| Matching Index (i) | | Cluster | | $D^{(i)}$ Statistics |
|---|---|---|---|---|
| | | A | B | |
| 1 | Group | a | b | $D^{(1)}$ =1.5+5=6.5 |
| 2 | | b | a | $D^{(2)}$ =0.4+3=3.4 |

| Counts | | Cluster | |
|---|---|---|---|
| | | A | B |
| Group | b | 423 | 12 |
| | a | 7 | 577 |

FIG. 7C

MANAGING PATIENT DEVICES BASED ON SENSOR DATA

BACKGROUND

Patients in hospitals and other medical care facilities frequently may be connected to, or otherwise monitored by, a plurality of different types of medical devices that monitor various bodily conditions. Examples of such monitoring devices include cardiac monitors, pulse oximeters, capnography monitors, respiratory rate monitors, neurological monitors, blood glucose monitors, fetal monitors, body temperature monitors, and hemodynamic monitors, to name a few. Each of these monitors may include one or more sensors and processing components that provide information that may often be expressed as a waveform or other quantitative result. In some cases, dozens or even hundreds of waveforms may be generated for each patient. A patient caregiver may examine the output of at least some of these monitors for determining suitable treatment for a patient.

Additionally, patients may be treated by medical devices that provide treatment for one or more medical conditions. Examples of such devices include ventilators, intravenous (IV) infusion pumps, pacemakers, chest tubes, feeding tubes, anesthetic machines, heart-lung machines, dialysis machines, urinary catheters, defibrillators, and the like. These devices also may provide waveforms and other electronic output indicative of their operation. For instance, a treatment device may often include monitoring capability as well, such as in the case of a ventilator that also provides respiratory rate and other respiratory information. Nevertheless, treatment with these devices is often managed based on predetermined treatment schedules and may be manually monitored by caregivers. As one example, medical ventilator usages for patients in an intensive care unit (ICU) may be manually monitored and recorded by caregivers on a regular basis, and the recorded information may be used in determining treatment efficacy and subsequent treatment plans. However, manual recording of clinical parameters determined from these devices and subsequent changes to the treatment may be inefficient and prone to error.

SUMMARY

Some implementations include arrangements and techniques for monitoring patients and/or managing patient devices based on sensor data. As one example, a service computing device may receive sensor data associated with a plurality of patient devices that are associated with a plurality of patients. The service computing device may further receive caregiver records corresponding at least partially to the sensor data. Indicators of at least two groups may be determined from the caregiver records, such a based on a selected subject. Further, the service computing device may determine a plurality of clusters from the sensor data. Based on the plurality of clusters and the at least two groups, the service computing device may determine an indication of a discrepancy in care for a patient of the plurality of patients. Based on the indication of the discrepancy in care, the service computing device may send at least one of a notification to a caregiver computing device, a notification to a monitoring computing device, or a control signal to one of the patient devices.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIGS. 7A-7C illustrate an example of determining patients associated with a discrepancy in care according to some implementations.

DETAILED DESCRIPTION

Figure 1:
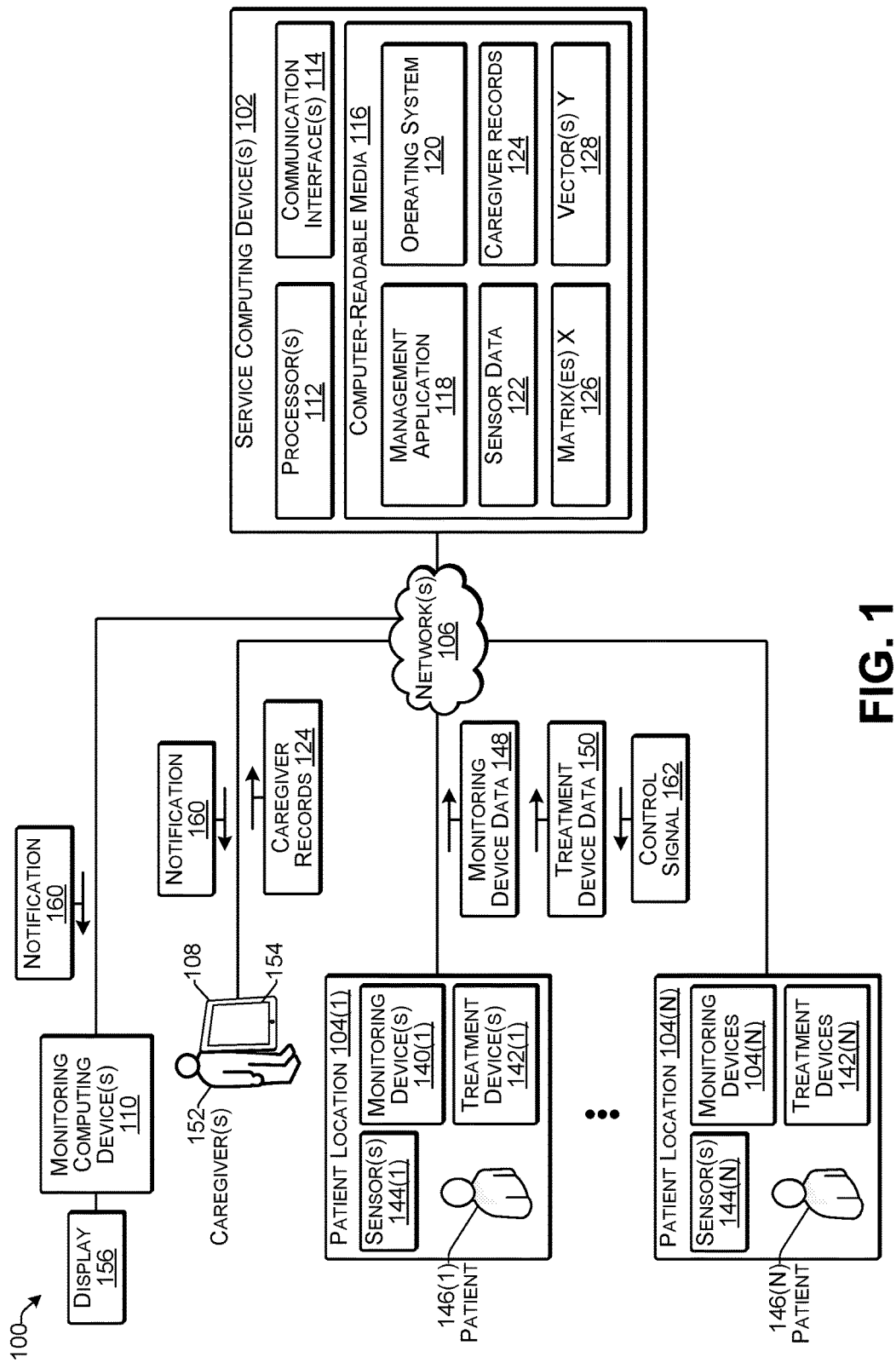
FIG. 1 illustrates an example architecture of a system able to detect a discrepancy in patient care and/or a discrepancy in a patient device according to some implementations.

Some implementations herein are directed to techniques and arrangements for determining a patient experiencing a discrepancy in care and/or automatically controlling one or more patient devices to monitor or treat the patient, such as at a medical care facility or other patient location. As one example, a service computing device may receive hundreds of physiologic waveform data from a plurality of patient devices associated with each patient of a plurality of patients. The service computing device initially may summarize the waveform data collected within a known time window for the plurality of patients to generate summary statistics for the time window. The summary statistics may be jointly analyzed using data reduction followed by unsupervised clustering. Manually entered caregiver records related to the patients and/or the patients' treatments may also be received by the service computing device from one or more caregiver computing devices, and may be used by the service computing device during the analysis. The results of the analysis may indicate one or more patients possibly experiencing a discrepancy in care and/or one or more treatment devices associated with the discrepancy in care. In some cases, the service computing device may send an alert or other notification to a caregiver, may send an alert or other notification to a central monitoring location, and/or may automatically control a setting of one or more patient devices, such as treatment devices, monitoring devices.

As mentioned above, manual records of clinical parameters of patients and patient treatments may be prone to errors. For example, records of medical ventilator usages by patients in an ICU may be manually recorded daily by caregivers, e.g., to document the number of times the ventilator is used by a patient, how long the ventilator is used each time, and so forth. However, it is not always readily apparent whether the ventilator is being used for an optimal amount of time for the particular patient, is being used at the correct settings, etc. Accordingly, implementations herein may concurrently analyze hundreds of waveforms to extract insights that are not apparent when using techniques that evaluate only one or a few waveforms at a time for a single patient. Furthermore, implementations herein do not require parametric assumptions or fitting parametric models. Accordingly, the examples herein may assist caregivers in reducing the risk of adverse events, reducing treatment cost, and reducing the patient's length of stay in the ICU or other treatment facility. Further, the information determined from the analysis may be used as feedback to one or more of the treatment devices or monitoring devices for patients that have been associated with a discrepancy in care.

Some examples include identifying patients with possible discrepancies in care based on analysis of received sensor data and caregiver records. For instance, a caregiver or a service computing device may specify a time window w and a time t of for which the sensor data and the caregiver records are analyzed for a plurality of patients. In some cases, the service computing may extract available waveforms, other sensor data, and caregiver records of all patients in an ICU or other care facility within a time frame t-w to t, and may summarize the waveform data and/or other sensor data into summary statistics. Furthermore, the service computing device may summarize the caregiver records for a selected treatment subject into groups of labels or other indicators for each patient within the time window w. Additionally, the service computing device may merge or otherwise associate the sensor data summary statistics and the summarized indicators from the caregiver records, such as based on patient identifiers (IDs) and selected time intervals. Using clustering techniques, the service computing device may detect patients with possible gaps in care as described additionally below. Accordingly, examples herein may use physiologic waveform data, other sensor data, and caregiver records to determine patients who may be experiencing a discrepancy in care. The determined information may be used to provide valuable insights to caregivers to identify possible discrepancies between caregiver records and actual care, so that timely follow-up and necessary adjustments can be performed. Additionally, or alternatively, the determined information may be used to control automatically one or more patient devices, such as a patient treatment device or a patient monitoring device. Accordingly, implementations herein may reduce the risk of adverse events and may reduce overall patient lengths of stay in the care facilities.

For discussion purposes, some example implementations are described in the environment of one or more computing devices receiving waveform data or other sensor data from patient monitoring devices and patient treatment devices, and further receiving caregiver records, and analyzing the received sensor data and caregiver records to provide feedback to a caregiver device or a patient device. However, implementations herein are not limited to the particular examples provided, and may be extended to other types of data, other types of patient environments, other system architectures, and so forth, as will be apparent to those of skill in the art in light of the disclosure herein.

FIG. 1 illustrates an example architecture of a system 100 able to detect a discrepancy in patient care and/or a discrepancy in patient devices according to some implementations. The system 100 includes at least one service computing device 102 that is able to communicate with a plurality of patient locations 104(1), ..., 104(N), such as through one or more networks 106. Further, the service computing device 102 may be able to communicate through the one or more networks 106 with one or more caregiver computing devices 108 and one or more monitoring computing devices 110.

In some examples, the service computing device 102 may include one or more servers, personal computers, or other types of computing devices that may be embodied in any number of ways. For instance, in the case of a server, the modules, other functional components, and at least a portion of data storage may be implemented on at least one server, such as in a cluster of servers, a server farm or data center, a cloud-hosted computing service, and so forth, although other computer architectures may additionally or alternatively be used. In the illustrated example, the service computing device 102 includes, or may have associated therewith, one or more processors 112, one or more communication interfaces 114, and one or more computer-readable media 116.

Each processor 112 may be a single processing unit or a number of processing units, and may include single or multiple computing units, or multiple processing cores. The processor(s) 112 can be implemented as one or more central processing units, microprocessors, microcomputers, microcontrollers, digital signal processors, state machines, logic circuitries, and/or any devices that manipulate signals based on operational instructions. For instance, the processor(s) 112 may be one or more hardware processors and/or logic circuits of any suitable type specifically programmed or configured to execute the algorithms and processes described herein. The processor(s) 112 can be configured to fetch and execute computer-readable instructions stored in the computer-readable media 116, which can program the processor(s) 112 to perform the functions described herein.

The computer-readable media 116 may include volatile and nonvolatile memory and/or removable and non-removable media implemented in any type of technology for storage of information such as computer-readable instructions, data structures, program modules, or other data. For example, the computer-readable media 116 may include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the service computing device 102, the computer-readable media 116 may be a tangible non-transitory medium to the extent that, when mentioned, non-transitory computer-readable media exclude media such as energy, carrier signals, electromagnetic waves, and/or signals per se. In some cases, the computer-readable media 116 may be at the same location as the service computing device 102, while in other examples, the computer-readable media 116 may be partially remote from the service computing device 102.

The computer-readable media 116 may be used to store any number of functional components that are executable by the processor(s) 112. In many implementations, these functional components comprise instructions or programs that are executable by the processor(s) 112 and that, when executed, specifically program the processor(s) 112 to perform the actions attributed herein to the service computing device 102. Functional components stored in the computer-readable media 116 may include a management application 118 and an operating system (OS) 120. The management application 118 may include one or more computer programs, computer-readable instructions, executable code, or portions thereof that are executable to cause the processor(s) 112 to performing various tasks, such as for monitoring patient status and/or for controlling patient treatment devices and monitoring devices. Additionally, the operating system 120 may control and manage various functions of the service computing device 102. In some cases, the functional components may be stored in a storage portion of the computer-readable media 116, loaded into a local memory portion of the computer-readable media 116, and executed by the one or more processors 112. Numerous other software and/or hardware configurations will be apparent to those of skill in the art having the benefit of the disclosure herein.

In addition, the computer-readable media 116 may store data and data structures used for performing the functions and services described herein. For example, the computer-readable media 116 may store sensor data 122, caregiver records 124, one or more matrixes X 126, and one or more vectors Y 128 that are used by the management application 118. For example, the management application 118 may receive the sensor data 122, such as waveform data and/or other sensor data, and the caregiver records 124, and may use this information to generate the matrix X 126 from the sensor data 122 and the vector Y 128 from the caregiver records 124 as discussed additionally below. Further, additional matrixes and/or other data structures (not shown in FIG. 1) may be generated from the matrix X 126 and the vector Y 128 and used for identifying patient having a discrepancy in care, as discussed below. The service computing device 102 may also include or maintain other functional components and data, which may include programs, drivers, etc., and other data used or generated by the functional components. Further, the service computing device 102 may include many other logical, programmatic, and physical components, of which those described above are merely examples that are related to the discussion herein.

The communication interface(s) 114 may include one or more interfaces and hardware components for enabling communication with various other devices, such as over the one or more networks 106. Thus, the communication interfaces 114 may include, or may couple to, one or more ports that provide connection to the network(s) 106 for communicating with the patient locations 104, the caregiver computing device(s) 108, and the monitoring computing device(s) 110. For example, the communication interface(s) 114 may enable communication through one or more of a LAN (local area network), WAN (wide area network), the Internet, cable networks, cellular networks, wireless networks (e.g., Wi-Fi) and wired networks (e.g., fiber optic, Ethernet, Fibre Channel), direct connections, as well as close-range communications such as BLUETOOTH®, and the like, as additionally enumerated elsewhere herein.

Patient locations 104(1), . . . , 104(N) may be patient rooms or any other location where a patient may be treated. In some examples, each of the patient locations 104(1), . . . , 104(N) may include a plurality of patient devices including one or more patient monitoring devices 140(1), . . . , 140(N), respectively, and one or more patient treatment devices 142(1), . . . , 142(N), respectively. Further, patient device sensors 144(1), . . . , 144(N) may be associated, respectively, with the monitoring devices 140(1), . . . , 140(N) and/or the treatment devices 142(1), . . . , 142(N), such as for detecting patient conditions and/or conditions of the monitoring devices 140 and/or the treatment devices 142. As one example, at least one patient 146(1), . . . , 146(N), may be located at each of the patient locations 104(1), . . . , 104(N), respectively, may be monitored by the monitoring device(s) 140(1), . . . , 140(N), respectively, and may be treated by the treatment device(s) 142(1), . . . , 142(N), respectively. Further, in some cases, a patient treatment device 142 may also be a patient monitoring device 140, and may include one or more sensors 144 for providing waveform data and/or other data about the patient's condition.

In some examples, each of the patient devices 140 and 142 may be able to communicate over the network 106 with the service computing device 102, such as to send monitoring device data 148 and treatment device data 150 to the service computing device 102. In other examples, one of the patient devices 140, 142 may include a computing device that collects the monitoring device data 148 from other monitoring devices 140 at the patient location 104, and collects the treatment device data 150 from the treatment devices 142 at the patient location 104, and that sends the monitoring device data 148 and the treatment device data 150 to the service computing device. In some examples, the monitoring device data 148 and the treatment device data 150 includes sensor data 122 obtained by the monitoring devices 140 and the treatment devices 142, respectively. For instance, as mentioned above, the patient monitoring devices 140 may include cardiac monitors, pulse oximeters, capnography monitors, respiratory rate monitors, neurological monitors, blood glucose monitors, fetal monitors, body temperature monitors, hemodynamic monitors, and/or various other types of monitoring devices. Further, the patient treatment devices 142 may include ventilators, intravenous (IV) infusion pumps, pacemakers, chest tubes, feeding tubes, anesthetic machines, heart-lung machines, dialysis machines, urinary catheters, defibrillators, and/or various other types of treatment devices.

The caregiver computing device 108 and the monitoring computing device 110 may be any suitable type of computing devices such as a desktop, workstation, server, laptop, tablet computing device, mobile device, smart phone, wearable device, or any other type of computing device able to send data over a network. In some cases, the caregiver computing device 108 and/or the monitoring computing device 110 may include hardware configurations similar to that described for the service computing device 102, but with different data and functional components to enable them to perform the various functions discussed herein. As one example, the caregiver computing device 108 may be a portable computing device, such as a tablet or laptop that a caregiver 152 carries when visiting patient locations 104, and the monitoring computing device 110 may be desktop computer, workstation, or server located at a central location, such as an ICU nursing station, floor reception area, or the like. The caregiver computing device 108 may include a display 154, and the monitoring computing device 110 may include a display 156. Numerous other variations will be apparent to those of skill in the art having the benefit of the disclosure herein.

In some cases, the caregiver 152, such as a nurse, physician, physician's assistant, attendant, or the like, may visit the patients 146 at the patient locations 104, and may use the caregiver computing device 108 to enter caregiver records 124. For instance, the caregiver records 124 may be related to the patient's condition, the settings or output of the patient monitoring devices 140, the settings or output of the patient treatment devices 142, and so forth. In some examples, the caregiver records 124 may be entered in a structured manner as structured data, such as by enabling the caregiver 152 to make selections in a form, or the like. Alternatively, in other examples, the caregiver records 124 may be handwritten records, typed records, or otherwise free-form data that may be analyzed by the service computing device 102 following receipt thereby. The caregiver records 124 may be sent to the service computing device 102 by each caregiver computing device 108, such as when entered by the caregiver 152, when the caregiver 152 has finished seeing a particular patient 146, at the end of the caregiver's shift, or the like.

The one or more networks 106 may include any type of network, including a local area network (LAN), such as an intranet; a wide area network (WAN), such as the Internet; a wireless network, such as a cellular network, a local wireless network, such as Wi-Fi, and/or short-range wireless communications, such as BLUETOOTH®; a wired network including fiber optics, Ethernet, Fibre Channel, or any other such network, a direct wired connection, or any combination thereof. Accordingly, the one or more networks 106 may include both wired and/or wireless communication technologies. Components used for such communications can depend at least in part upon the type of network, the environment selected, or both. Protocols for communicating over such networks are well known and will not be discussed herein in detail. Accordingly, the service computing device 102, the patient locations 104, the caregiver device(s) 108, and the monitoring computing device(s) 110 are able to communicate over the one or more networks 106 using wired or wireless connections, and combinations thereof.

In the example of FIG. 1, the management application 118 may be executed to receive the monitoring device data 148, the treatment device data 150, and the caregiver records 124. As mentioned above, the monitoring device data 148 and/or the treatment device data 150 may include the sensor data 122, such as waveform data, that may be used by the management application 118 in conjunction with the caregiver records 124 to analyze the condition of each patient 146. Furthermore, in some examples, the sensor data 122 and/or the caregiver records 124 may be indicative of a condition of a monitoring device 140 or a treatment device 142. In some examples, the management application 118 may first summarize hundreds of waveform data and other sensor data 122 collected for a plurality of patients 146 to generate summary statistics in the matrix X 126. The summary statistics may be jointly analyzed using a data reduction technique followed by unsupervised clustering. The caregiver records 124 may be used to generate the vector Y 128 and may be used during the analysis to detect patients possibly experiencing a discrepancy in care and/or treatment devices associated with the discrepancy in care. When such a condition is detected, the management application 118 may send an alert or other notification 160 to at least one of the caregiver device 108 or the monitoring computing device 110. For instance, the notification may be presented on the display 154 and/or 156 respectively, to notify the caregiver 152 or other medical personnel of the condition.

In addition, in some cases, the management application 118 may automatically adjust a setting of one or more patient devices 140, 142, such as by sending a control signal 162 for controlling a particular patient treatment device 142 or a particular patient monitoring device 140. For example, suppose that a treatment device 142 is an IV infusion pump, and the analysis shows that the pump is not delivering enough fluids to the patient. The control signal 162 may control the infusion pump to increase the flow of fluids to the patient. As another example, the control signal 162 may control a monitoring device 140, such as to turn on a particular monitoring device 140 that may not have been on, but which may be used to further analyze a detected patient condition or other care discrepancy.

As another example, the analysis data may indicate a discrepancy between the caregiver records and the patient's actual condition. For example, suppose that the caregiver records indicate that a treatment device 142, such as the patient's ventilator, is on, but the analysis results indicate that the treatment device 142 belongs to a cluster of devices that are not on at that time. Based on this determination, the management application 118 may send the control signal 162 to turn on the ventilator, and/or may send the notification 160 to the caregiver computing device 108 and/or the monitoring computing device 110 to notify the caregiver 152 that the ventilator is not on. On the other hand, if the caregiver records indicate that the ventilator is off, but the analysis results indicate that the ventilator belongs to a cluster of devices that are on at that time, the management application 118 may send the control signal 162 to turn off the ventilator, and/or may send the notification 160 to the caregiver computing device 108 and/or the monitoring computing device 110 to notify the caregiver 152 that the ventilator is on.

Figure 2:
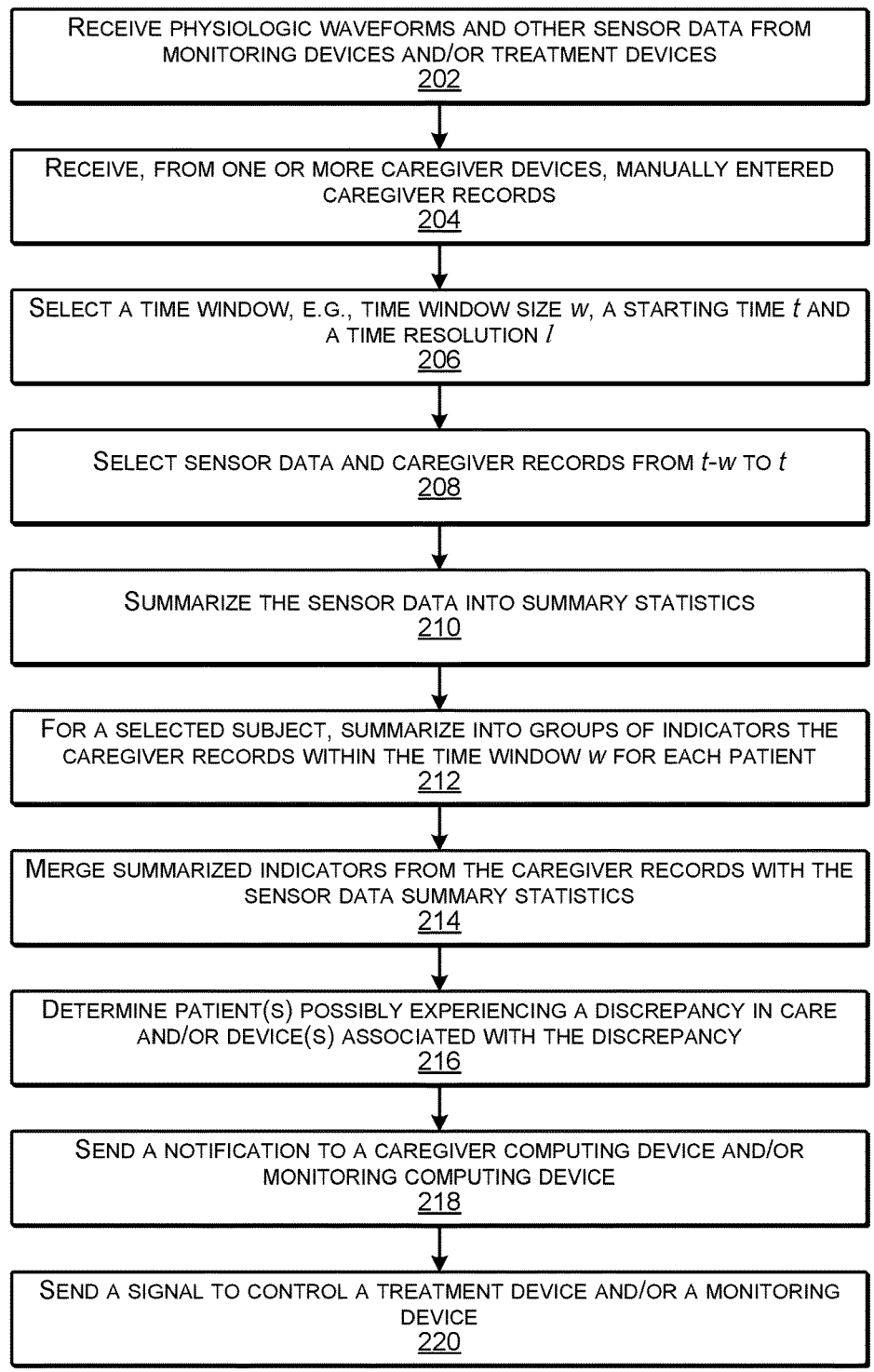
FIG. 2 is a flow diagram illustrating an example process for detecting a patient condition and/or for controlling a patient device according to some implementations.
Figure 3:
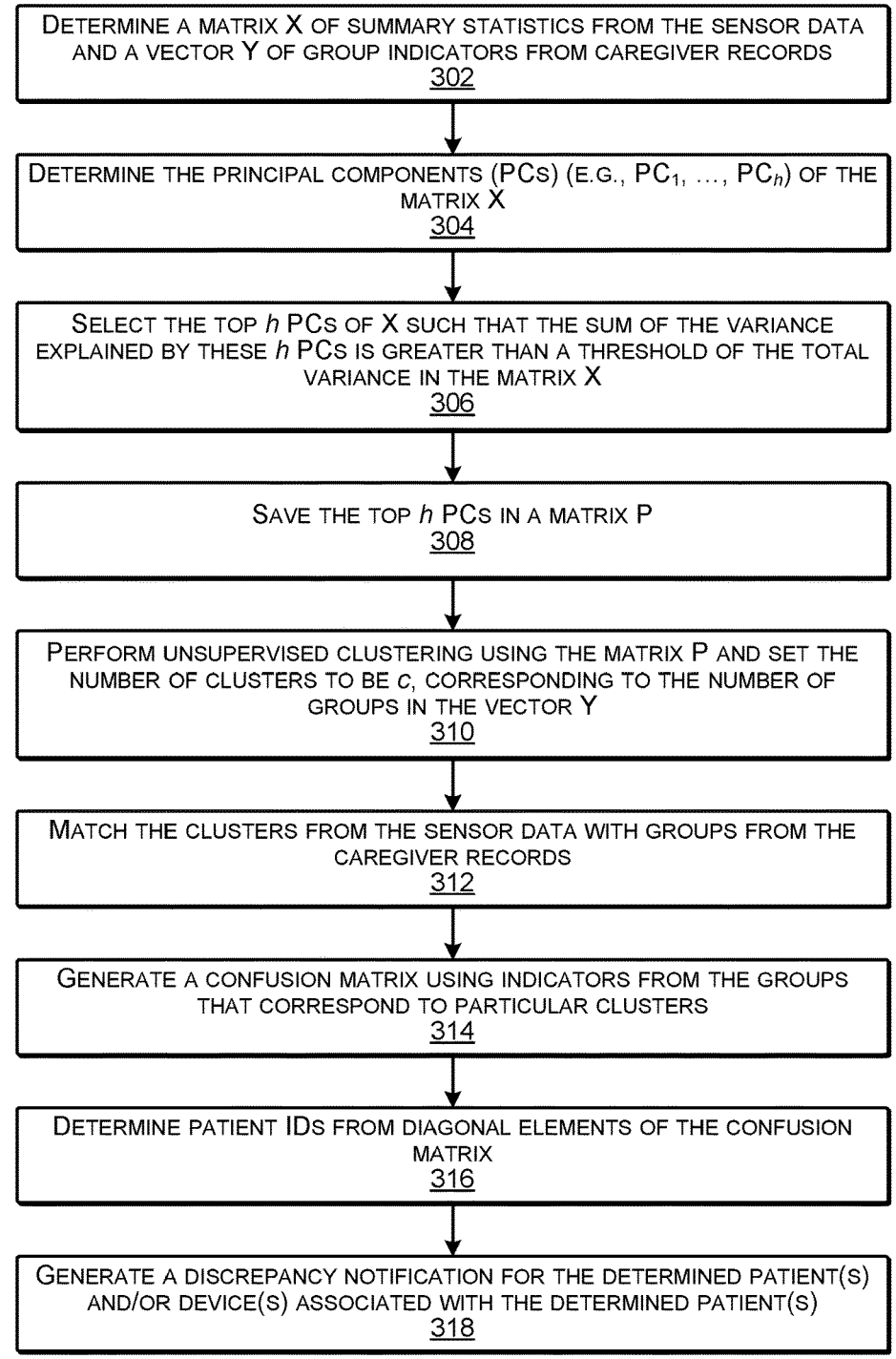
FIG. 3 is a flow diagram illustrating an example process for detecting a patient experiencing a discrepancy in care and/or a patient device associated with the discrepancy according to some implementations.

FIGS. 2 and 3 are flow diagrams illustrating example processes according to some implementations. The processes are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the processes are described with reference to the environments, frameworks and systems described in the examples herein, although the processes may be implemented in a wide variety of other environments, frameworks and systems.

FIG. 2 is a flow diagram illustrating an example process 200 for detecting patient conditions and/or controlling treatment devices according to some implementations. In some examples, the process 200 may be executed by the service computing device 102 or other suitable computing device.

At 202, the computing device may receive physiologic waveforms and other sensor data from monitoring devices and/or treatment devices. For example, the computing device may receive as many as hundreds of different waveforms for each patient from a plurality patient devices associated with each patient.

At 204, the computing device may receive manually entered caregiver records from caregiver devices. For example, a nurse or other caregiver may manually enter information in a structured format, such as a form provided on a tablet computing device or the like. Alternatively, the computing device may receive freeform data, and may perform analysis on the received freeform data to extract information relevant to particular treatment subjects.

At 206, the computing device may select a time window, e.g., time window size w (e.g., a number of hours), a starting time t and time resolution 1. For instance, the time window start time and size may be based at least in part on the treatment subject that is being analyzed.

At 208, the computing device may select sensor data and caregiver records from t-w to t. In some examples, a user may instruct the computing device regarding a desired recent time interval and/or a desired treatment subject for which to conduct an analysis to determine if there has been a discrepancy in care for one or more patients.

At 210, the computing device may summarize the sensor data into summary statistics. For instance, the computing device may summarize waveform data by generating one of more values to represent the waveform over a period of time. Examples of such representative values may include a mean, a median, a standard deviation, a count, a high measurement, a low measurement, or the like, depending on the type of waveform data.

At 212, the computing device may summarize the caregiver records for a selected treatment subject into groups of indicators for each patient within the time window w. For example, the indicators may be labels or other quantified indicators of particular manually entered records such that there are at least two groups of indictors for each patient treatment subject. For instance, with respect to the treatment subject of ventilator compliance, there may be two groups of indicators-a first group in which the indicator is "on" and a second group in which the indicator is "off". Similarly, with respect to the subject of infusion pump compliance, there may be multiple different groups of indicators, such that each different group of indicators corresponds to a different pump flowrate setting, e.g., in ml/hr, such as 0 ml/hr, 0.075 ml/hr, 0.125 ml/hr, and so forth. Accordingly, the indicators for a particular group are related to the treatment subject to which the group is related. In some examples, the caregiver records may include data related to individual patients manually entered by a caregiver to at least one of a structured data format or a freeform data format. In the case of the structured data format, the caregiver may enter the data related to the patient by filling out a form, checking boxes in a graphic user interface, entering answers to standardized questions, or the like. In the case of a freeform data format, the caregiver may provide handwritten, dictated, or typed notes, and the summarizing of the caregiver records may include using artificial intelligence techniques to extract, from the freeform data, quantifiable information that is related to a particular subject related to patient treatment.

At 214, the computing device may merge the groups of indicators from the caregiver records with the sensor data summary statistics. For instance, each vector Y for each different subject may include the two or more groups of indicators for that subject. Examples of subjects in which a caregiver may be interested may include ventilator compliance, infusion pump compliance, dialysis activity, blood sugar compliance, pacemaker activity, and so forth. Accordingly, a different vector Y may be generated for each of these different treatment subjects or other treatment subjects, depending on the actual content of the caregiver records.

At 216, the computing device may determine patients experiencing a discrepancy in care and/or devices associated with the discrepancy. For example, the computing device may merge or otherwise associate the summarized sensor data with the summarized caregiver records.

At 218, the computing device may send a notification to a caregiver computing device and/or monitoring computing device. For instance, the computing device may send a notification to cause an alert to be presented on a display of the caregiver device and/or a display of the monitoring computing device. The notification may alert the caregiver to take corrective action and/or may perform other appropriate intervention.

At 220, the computing device may send a signal to control a treatment device and/or a monitoring device. As one example, the computing device may send a control signal to control a treatment device at the patient location. For instance, based on the patient ID of the patient identified as having a discrepancy in care, the computing device may determine the patient location, and based on the treatment subject, may determine one or more treatment devices or monitoring devices to control in response to the discrepancy in care. For instance, the computing device may turn on, turn off, or adjust a setting of a patient device, such as a treatment device or a monitoring device. A notification to a caregiver may also be sent in addition to sending the control signal to patient device. Further, in some examples, the control signal may only be sent to the patient device in certain situations, such as if the detected discrepancy in care is exceeds a threshold level of urgency.

FIG. 3 is a flow diagram illustrating an example process 300 for detecting a patient experiencing a discrepancy in care and/or a patient device associated with the discrepancy according to some implementations. In some examples, the process 300 may be executed by the service computing device 102 or other suitable computing device.

At 302, the computing device may determine a matrix X of summary statistics from the waveforms or other sensor data, and a vector Y including group indicators obtained from caregiver records. For example, as discussed above, there may be two or more different groups in each vector Y, corresponding to the treatment subject of the vector Y. For instance, if the treatment subject of the vector Y is ventilator compliance, a first group of indicators may be "on" and a second group of indicators may be "off". The values of the indicators and the number of groups of indicators may differ in some examples based on the different treatment subjects of the different vectors Y.

At 304, the computing device may determine the principal components (PCs) (e.g., $PC_1, \ldots, PC_k$) of the matrix X. For instance, the computing device may apply principal component analysis (PCA) to the matrix X to reduce the dimensions of the matrix X to enable faster processing of the sensor data. Further, other techniques for data reduction may be used in place of PCA in some examples. Additionally, in other examples, PCA and other data reduction techniques are not used and the summarized data may be analyzed instead.

At 306, the computing device may select the top h PCs of the matrix X such that the sum of the variance corresponding to these top h PCs is greater than a threshold value for the total variance in the matrix X. For example, the several top PCs may contain a large percentage of the useful information in the matrix X since the column vectors of the matrix X are likely to be high-dimensional and highly correlated. Therefore, selecting the top h PCs of the matrix X may substantially reduce the computational burden and avoid collinearity, while still preserving most of the information from matrix X.

At 308, the computing device may save the top h PCs in a matrix P. For instance, the computing device may generate the matrix P of PCs that will be used during subsequent clustering.

At 310, the computing device may perform unsupervised clustering using the matrix P and set the number of clusters to be c, corresponding to the number of groups in the vector Y. As one example, the computing device may use the k-means algorithm to determine c clusters by plotting entries from the selected PCs in the matrix P. Further, in the case in which PCA or other data reduction technique are not used, the clustering may be performed for the matrix X.

At 312, the computing device may match the clusters determined from the summarized and converted waveform data with groups from the caregiver records. For example, the groups of indicators from the selected vector Y may be matched with the clusters, and differences between the centroids of the clusters and the centroids of the groups may be used to determine patients who may have experienced possible discrepancies in care.

At 314, the computing device may generate a confusion matrix using the indicators from the groups that correspond to the particular clusters. For instance, the confusion matrix may indicate which indicators correspond to which cluster so that the computing device is able to determine which patients possibly experienced a discrepancy in care at a specific time, and which did not.

At 316, the computing device may determine patient IDs from diagonal elements of the confusion matrix. As one example, the confusion matrix may match indicators from the groups in Y with clusters identified from matrix P of PCs so that the computing device is able to determine which patients possibly experienced a discrepancy in care, and which patients did not.

At 318, the computing device may generate a discrepancy notification for the determined patient(s) and/or patient device(s) associated with the determined patient(s). For example, the computing device may send a notification including a patient ID, and the subject of the possible discrepancy in care to the caregiver associated with the patient and/or to a central monitoring computing device. Additionally, or alternatively, the computing device may send a control signal to a patient treatment device and/or patient monitoring device at the patient location of the patient who may have experience a discrepancy in care.

The example processes described herein are only examples of processes provided for discussion purposes. Numerous other variations will be apparent to those of skill in the art in light of the disclosure herein. Further, while the disclosure herein sets forth several examples of suitable frameworks, architectures and environments for executing the processes, the implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Figure 4:
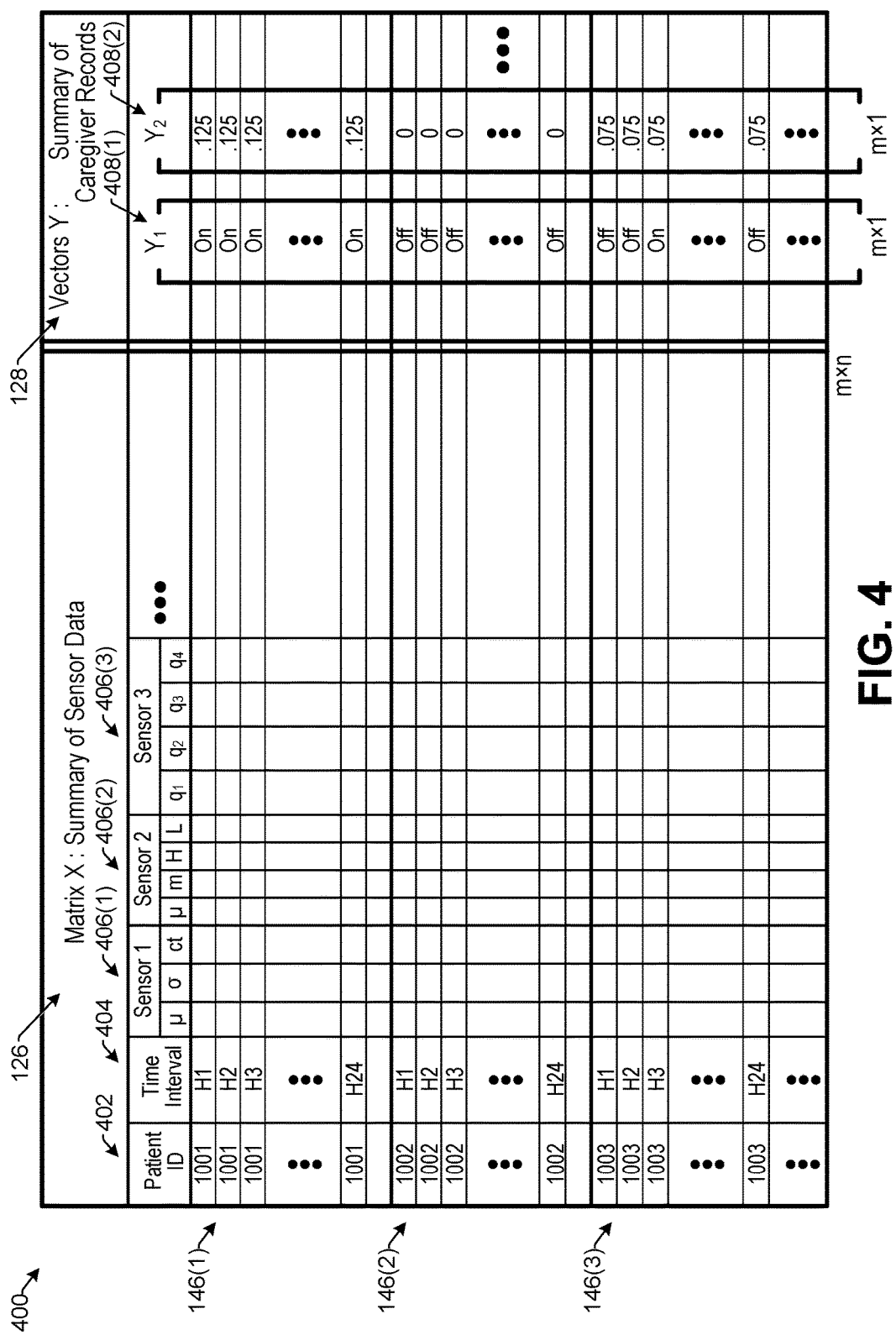
FIG. 4 illustrates an example of summarized sensor data and caregiver records according to some implementations.

FIG. 4 illustrates an example 400 of summarized sensor data and caregiver records according to some implementations. In this example, the physiologic waveform data and other sensor data received from the sensors at the patient locations and the caregiver records are summarized for a time window w of that is divided into time intervals. The sensor data received over the time window w, such as individual waveforms and/or other data from a plurality of sensors are summarized in a data structure, such as the matrix X 126. In addition, the caregiver records for the same time window w are summarized in a data structure, such as one or more vectors Y 128. The matrix X 126 includes the received sensor data for a plurality of patients identified by respective patient IDs 402. Matrix X 126 further includes entries to indicate a time interval 404, and sensor data from a plurality of respective sensors 406(1), 406(2), 406(3), . . . . In addition, the vectors Y 128 may be expressed for different treatment subjects such as a first vector $Y_1$ 408(1), a second vector $Y_2$ 408(2), and so forth. For instance, the different vectors $Y_1$, $Y_2$, etc., each may correspond to different treatment subjects the may be of interest to a caregiver, e.g., ventilator status, IV status, pacemaker status, and the like.

The matrix X 126 may include m×n entries, where m is the number of rows and n is the number of columns. Each vector Y may include m×1 entries, i.e., one entry for each row in the matrix X. In this example, suppose that there are 1000 patients, and thus, the matrix X includes entries for a first patient 146(1), a second patient 146(2), a third patient 146(3), and so forth, up to the 1000th patient (not shown in FIG. 4). Further, in this example, suppose that there may be up to 300 different sensors 406 for each patient. Each sensor 406 may provide a different waveform data or other sensor data. In addition, suppose in this example that the selected time window w is one day and that the selected time interval is one hour.

Depending on the type of sensor and the type of received sensor data, the sensor data may be summarized into one or more values that represent the waveform or other received sensor data for each one hour interval. As one example, after k physiologic waveforms of x patients from time t-w to time t have been determined, the data may be stratified according to $$r = \frac{w}{l}$$

time intervals, where r is a unitless number indicating the number of time intervals over which the analysis is being conducted, and l is the specified time resolution. For instance, l may be a day, an hour, a half hour, 15 minutes, or any other desired time interval. l can have the same unit as w to obtain the unitless quantity r, which is the number of time intervals within the selected time window w. Thus, in this example, r=24, i.e., one day (24 hours) divided by 1 hour.

For each time interval of the r time intervals, summary statistics may be calculated for each waveform or other received sensor data of each sensor for every patient of the x number of patients. In this example, there are 300 sensors that may be associated with each patient and the sensor data received over each of the time interval for each of those sensors may be summarized for the time interval and these summary statistics may be stored into the matrix X. Depending on the type of sensor data, the summary statistics may include, for example, at least one of a mean, a count, a standard deviation, a median, a high point, a low point, or other meaningful indicator of the sensor data within the time interval, For example, suppose that the first sensor 406(1) is a respiratory rate sensor. The waveform data received from the respiratory rate sensor may be summarized as a mean μ, a standard deviation σ, and a count ct for the patient's respiration for each time interval. Thus, the waveform data received from the respiratory rate sensor over a particular hour may be summarized as breaths per minute; standard deviation of breaths per minute, and total number of breaths taken over that hour. As another example, suppose that second sensor 406(2) is a sensor for which the mean, the median, the highest value, and the lowest value are meaningful. In addition, suppose that third sensor 406(3) is a sensor for which a number of occurrences of events, e.g., $q_1$, $q_2$, $q_3$, $q_4$, is meaningful. Thus, the waveform data and other sensor data for the plurality of sensors 406 may be summarized for each time interval.

In addition, the caregiver records may be summarized into the one or more vectors Y 128. Each vector Y may include m elements, i.e., one summarized sensor data entry for each time interval r in the matrix X. Elements of the vector Y are indicators of two or more groups of indicators for a selected treatment subject for each patient in every time interval. For example, the group labels may be for recorded ventilator usage, compliance status of a specific assessment, IV pump status, and so forth. In the illustrated example, the first vector $Y_1$ 408(1) may represent the condition of a patient's ventilator and may include two groups of indicators, namely "on" or "off", although additional or different groups of indicators may be included in other examples. Further, the second vector $Y_2$ 408(2) may represent the condition of a patient's IV pump, and further, supposed the second vector $Y_2$ includes five groups of indicators, namely, 0 ml/hr, 0.075 ml/hr; 0.125 ml/hr, 0.250 ml/hr, and 0.350 ml/hr. Thus, each vector Y may have two or more different groups of indicators, depending on the treatment subject of the particular vector Y. As discussed below, the contents of the data structures X and Y serve as an input for determining patients that may be experiencing a discrepancy in care.

Figure 5:
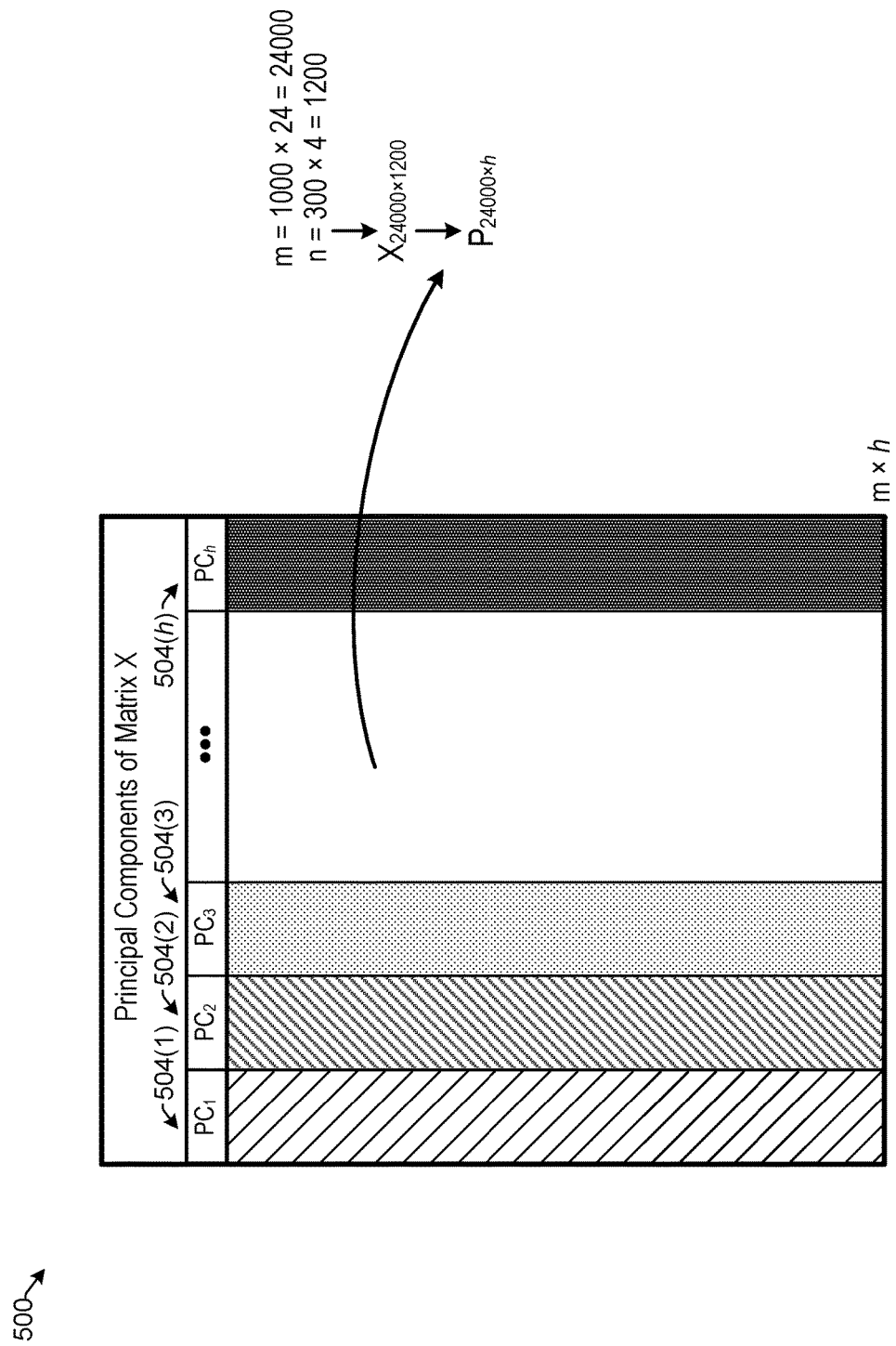
FIG. 5 illustrates an example of determining and selecting principal components of the matrix X according to some implementations.

FIG. 5 illustrates an example 500 of determining and selecting principal components of the matrix X according to some implementations. Implementations herein may detect outlying patients with a possible discrepancy in care within the time window w, given the matrix X and the vector Y described above. However, the entire matrix X typically may be too large and too noisy to easily process and obtain meaningful information. Accordingly, some examples herein include generating k principal components (PCs) of X, also referred to as the k eigenvectors of the covariance matrix of the matrix X. Covariance is a measure of how much two random variables change together. For instance, if the greater values of one variable mainly correspond with the greater values of the other variable, and the same holds for the lesser values, i.e., the variables tend to show similar behavior, the covariance is positive. A covariance matrix is a matrix whose element in the i, j position is the covariance between the $i^{th}$ and $j^{th}$ elements of a random vector, where the random vector is a random variable having multiple dimensions. Each element of the random vector may be a scalar random variable, and each element may have either a finite number of observed empirical values, or a finite or infinite number of potential values. The potential values may be specified by a theoretical joint probability distribution.

Principal component analysis (PCA) is a statistical procedure that uses an orthogonal transformation to convert a set of observations of possibly correlated variables into a set of values of linearly uncorrelated variables called the principal components (PCs). The number of PCs is less than or equal to the number of original variables. This transformation may be defined so that the first PC has the largest possible variance (i.e., accounts for as much of the variability in the data as possible). Each succeeding PC may, in turn, have the highest variance possible under the constraint that the particular PC is orthogonal to the preceding PCs. The resulting vectors are an uncorrelated orthogonal basis set. The PCs are orthogonal because they are the eigenvectors of the covariance matrix of X.

In the illustrated example, PCA may be used to generate a plurality of PCs. The top h PCs may be selected such that the sum of the variance explained by these h PCs is greater than 80 percent (or other selected threshold percentage) of the total variance of the matrix X and saved in a matrix P 502. Thus, in this example, the top h PCs, e.g., $PC_1$ 504(1), $PC_2$ 504(2), $PC_3$ 504(3), . . . , $PC_h$ 504 (h) are saved in the matrix P 502, such that the matrix may be expressed as $P_{m \times h} = [PC_1, PC_2, \ldots, PC_h]$. The reasoning underlying the use of PCA is that column vectors of the matrix X are likely to be high-dimensional and highly correlated. Selecting the top h PCs of the matrix X may substantially reduce the computational burden and avoid collinearity, while still preserving most of the information from matrix X.

For the example matrix X discussed with respect to FIG. 4, suppose that the sum of the variance of the first two PCs, $PC_1$ and $PC_2$, meets or exceeds the threshold percentage (e.g., 80 percent of the total variance of matrix X). Then, h=2 and for a matrix X having 24000 rows m (e.g., 24 hours for each of 1000 patients) and 900 columns n (e.g., 300 sensors with an average of 4 summary statistics values per sensor), the size of the matrix for processing may be reduced from $X_{24000 \times 900}$ to $P_{24000 \times 2}$. For instance, with more of the total variance concentrated in the first few PCs compared to the same noise variance, the proportionate effect of the noise is less, and the first several PCs may achieve a higher signal-to-noise ratio. Accordingly, using PCA can have the effect of concentrating much of the signal into the first few PCs, which can be captured by dimensionality reduction, while the later PCs may be dominated by noise, and so disposed of without great loss of accuracy in the final determination of patients possibly experiencing a discrepancy in care. Numerous open source PCA calculation tools are readily available from multiple sources, such as SOURCEFORGE MEDIA™ of LaJolla, Calif.; PLOS™ of San Francisco, Calif.; GNU PSPP available from the Free Software Foundation, Inc., of Boston, Mass., to name a few. Furthermore, PCA is not the only technique for converting the matrix X to a smaller size and/or dimension for performing the clustering. For instance, other techniques that may be used reduce the matrix X include factor analysis, singular value decomposition, eigen decomposition, and so forth.

In some examples, after calculating the matrix P, the matrix X may be discarded and/or stored to a storage location to free up memory in the service computing device. Further, the matrix P may be determined independently of any vector Y, and the caregiver records for determining one or more vectors Y may be received and/or determined at a later point in time after the matrix P has been determined. For instance, a first caregiver may be interested in a first subject, such as whether the patients' ventilators are in compliance, while a second caregiver may be interested in a second subject, such as whether the patients' IV pumps are in compliance. Thus, a separate vector Y may be generated from the caregiver records for each of these subjects, and the service computing device may identify any patients that appear to have experienced a discrepancy in care.

Figure 6:
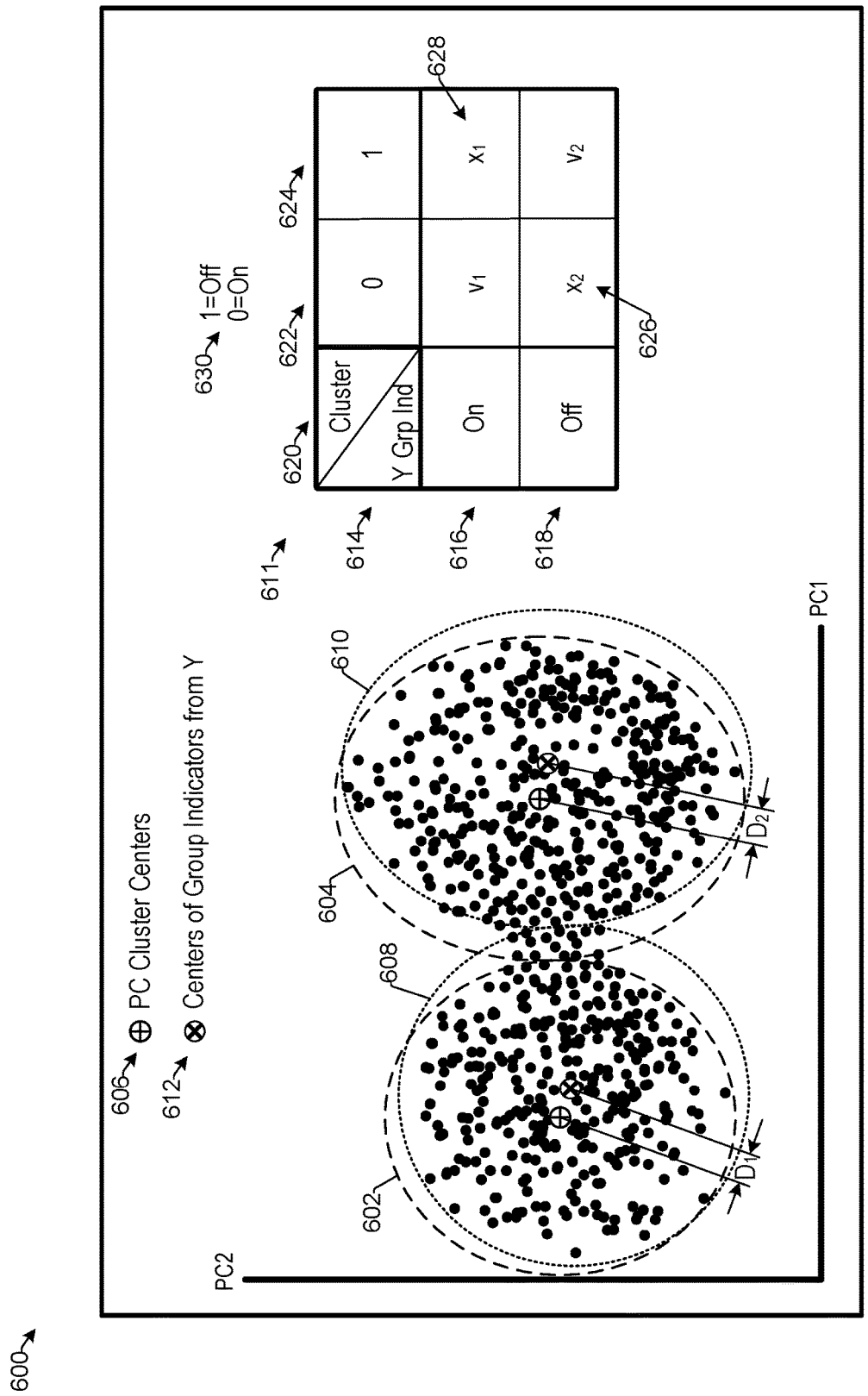
FIG. 6 illustrates an example of determining clusters of the summarized and converted sensor data according to some implementations.

FIG. 6 illustrates an example 600 of determining clusters of the summarized and converted sensor data according to some implementations. For example, after the matrix P has been generated as discussed above with respect to FIG. 5 by converting the summarized data to principal components, the management application 118 may determine clusters from the matrix P using an unsupervised clustering algorithm, such as the k-means clustering algorithm, or other known clustering techniques. For instance, the k-means clustering algorithm may be used to classify a given data set through a certain number of clusters (assume k clusters) fixed a priori. The number of clusters k are determined based on the number of groups in the matrix Y. The algorithm may define k centers, one for each cluster. These centers may be placed in a calculated manner because different locations may cause different results. As one example, the algorithm may initially place the centers as far away from each other as possible. Next, each point belonging to a given data set may be associated to the nearest center. When no additional points are pending, this step is complete and an early group age is determined. Next, k new centroids may be determined as barycenters of the k clusters determined in the previous step. After the k new centroids are determined, a new binding may be performed between the same data set points and the nearest new center. Additional iterations may be performed, and the k centers may change respective locations step-by-step until the k centers do not move any more. The number of clusters c may be the same as the number of unique values, i.e., the number of groups of indicators in the corresponding vector Y, summarized from caregiver records, as discussed above with respect to FIG. 4.

In the example of FIG. 6, suppose that the processing is being performed for the first vector $Y_1$ 408(1) in FIG. 4, e.g., for a treatment subject of examining the patients' ventilator conditions. In this example, the vector $Y_1$ includes two groups of indicators, namely ventilator "on" or ventilator "off". For example when the caregiver goes to each patient location, the caregiver may enter manually in the records for that patient whether the patient has a ventilator that is on, or if the ventilator is off (i.e., the patient is not currently connected to a ventilator). For example, some patients may be connected to a ventilator fulltime, while others may receive periodic ventilation, while still others may not be connected to a ventilator at all. In some cases, the caregiver may indicate that a patient is connected to a ventilator, but the summarized data of matrix X may indicate that the patient is not actually connected to a ventilator, is not properly connected to the ventilator, the ventilator has been turned off, or the like. Thus, the service computing device may detect this discrepancy and may send a notification that the particular patient may be at risk or may otherwise be experiencing a discrepancy in care, and/or, the service computing device may turn on the ventilator if the ventilator was turned off, or the like.

Clusters from the selected PCs may be matched with groups from a particular caregiver vector Y to determine patients experiencing a discrepancy in care. In the illustrated example, the values from the matrix P (the top h PCs, e.g., PC1 and PC2 in this example) are clustered using the k-means clustering algorithm or other clustering algorithm, as discussed above, to provide a first cluster 602 and a second cluster 604. The plotted cluster data from the PCs and the groups of indicators from the caregiver records are aligned into pairs by first calculating the center of each cluster $(C_1, C_2, \ldots, C_c)$, where $C_i = (C_{j1}, \ldots, C_{js})'$ is an h-dimensional vector of the principle component scores of the center of the $j^{th}$ cluster. The respective center of each of the PC clusters 602 and 604 is indicated by symbol 606 within each cluster 602 and 604.

Next the center of each group of indicators from vector $Y_1$, $(G_1, G_2, \ldots, G_c)$, is determined, where $G_j = (G_{j1}, \ldots, G_{js})'$ is an h-dimensional vector of principle component scores of the center of the $j^{th}$ group from the caregiver records. In this example, since the number of groups is two, there are two PC clusters 602 and 604, and two groups of indicators in Y, i.e., groups 608 and 610. In other examples, there may be more than two clusters and a corresponding number of groups of indicators in the vector Y.

The centers of the groups may be determined based on respective barycenters of the respective groups. In FIG. 6, the respective centers of the groups 608 and 610 are indicated by the symbol 612. The distances $D_1$ and $D_2$ between the centers of the clusters 602, 604 and the centers of the groups 608, 610, respectively, from all possible c! alignments may be calculated. The smallest overall distance D between a center 606 of a cluster and a center 612 of a group may be determined, which is described mathematically in the following equation 1:

$$\operatorname*{argmin}_{i \in \{1 \ldots c!\}} D^{(i)} \quad (EQ1)$$

where $D^{(i)} = \Sigma_{j=1}^{c} d_j^{(i)}$, and $d_j^{(i)}$ is the Euclidean distance between the center of the $j^{th}$ cluster and its aligned group from the $i^{th}$ alignment from the c! possibilities of aligning c groups to c clusters. Consequently, $d_j^{(i)}$ can be written as the following equation 2:

$$d_j^{(i)} = d(C_j, G_{j^{(i)}}) = \sqrt{\sum_{k=1}^{h} (C_{jk} - G_{j^{(i)}_k})^2} \quad (EQ2)$$

where $G_{j^{(i)}}$ is the vector of the center of the group that is aligned to the $j^{th}$ cluster in the $i^{th}$ alignment.

Next, a confusion matrix 611 may be generated from the clusters 602, 604 and using the indicators from the Y groups 608, 610. In this example, two groups of indicators are included in the caregiver records i.e., in the ventilator "on" or "off" indicator groups of vector Y. The confusion matrix 611 includes the Y group indicators 614 on one side (i.e., "On" indicator 616 and "Off" indicator 618) and the PC cluster identifier information 620 on the other side, (i.e., "0" 622 or "1" 624). Using techniques discussed additionally below, outlying patients may be identified from the diagonal cells 626 and 628 of the confusion matrix 611 as shown in this example. For instance, as indicated at 630, in this example, the "off" indicator matches with "1" in the clusters and the "on" indicator matches with "0" in the clusters. Accordingly, the data points in 626 and 628 in which "off" matches with "0" and "on" matches with "1", respectively, may indicate, for example, for particular patient IDs, that either the ventilator is not on when it should be, or is on when it should not be. For instance, the values $v_1$ and $v_2$ may correspond to the number of patients where the care appears normal, and $x_1$ and $x_2$ may correspond to the number of patients where there appears to be a discrepancy in care. Accordingly, the confusion matrix enables the management program to determine which patients in the clusters have experienced a discrepancy in care, and which have not.

FIGS. 7A-7C illustrate an example of determining patients associated with a discrepancy in care according to some implementations. FIG. 7A illustrates an example distance matrix 702 of distances between the center of a cluster and the center of corresponding group when the number of clusters c=2. For example, column A 704 and column B 706 are the identifiers of respective clusters from unsupervised clustering results of the summarized sensor data. Rows a 708 and b 710 correspond to the labels or other indicators from two groups of indicators summarized from the caregiver records (such as, for example, a first group of "on" indicators, and a second group of "off" indicators, or other suitable indicators, depending on the treatment subject associated with the vector Y). The values in the distance matrix 702 may be the Euclidean distance between centers of the clusters and the centers of the respective groups. For example, 1.5 is the Euclidean distance between the center of cluster A determined from clustering the sensor data and the center of group a determined from the caregiver records. Similarly, 0.4 is the Euclidean distance between the center of cluster A determined from clustering the sensor data and the center of group b determined from the caregiver records; 3 is the Euclidean distance between the center of cluster B determined from clustering the sensor data and the center of group a determined from the caregiver records; and 5 is the Euclidean distance between the center of cluster B determined from clustering the sensor data and the center of group b determined from the caregiver records.

FIG. 7B illustrates a data structure 720 for performing matching according to some implementations. The data structure 720 indicates all possible matching plans and their $D^{(i)}$ statistics, including a first matching plan 722 and a second matching plan 724. In this example, matching plan 724 in which i=2 is selected because $D^{(2)}<D^{(1)}$. In particular, as indicated at 726, $D^{(2)}$ is determined by adding the Euclidian distance for Ab and the Euclidian distance for Ba determined in the distance matrix 702, i.e., 0.4+3=3.4. Thus, $D^{(2)}$ is less than $D^{(1)}$, which is determined by adding the Euclidian distances for Aa and Bb, i.e., 1.5+5=6.5. Accordingly, as discussed below, a confusion matrix 740 may be generated based on the matching of Ab and Ba according to the minimum distance. The confusion matrix may enables the management program to determine which PC cluster corresponds to which group of indicators in the vector Y, and thus, which patients may have experienced a discrepancy in care, and which patients have not.

FIG. 7C illustrates an example of the confusion matrix 740 generated based on the matching plan 724 of FIG. 7B according to some implementations. In this example, the confusion matrix 740 may be used to detect patients with a possible discrepancy in care. For instance, as indicated at 742 and 744, respectively, entries in which A matches b, and B matches a, indicate normal care. On the other hand, as indicated at 748 and 750, respectively, entries in which A matches a, and B matches b, indicate a discrepancy in care for particular patients. Consequently, in this example, 12+7=19 patients are identified to have possible discrepancies in care, such as possible inconsistencies between caregiver records and the physiologic waveforms. Accordingly, the outlying points may be determined from the confusion matrix 730 generated from the cluster identifiers and from the groups of indicators in vector Y summarized from the caregiver records. The patient identifiers corresponding to the outlying points may be determined from the matrix P or from correlating the vector Y with the matrix P. After the set of outlying patients has been identified, these patients may be classified as "possibly experiencing a discrepancy in care" within the time window w and this information may be reported to caregivers with the respective patient IDs or other patient identifying information.

Further, in some examples, a particular patient device corresponding to the subject to which the vector Y is related may be controlled by the service computing device, as discussed above. For example, if the subject of the vector Y is IV infusion pump compliance, and the discrepancy in care shows that the patient is receiving an infusion a higher rate than indicated in the caregiver notes, the service computing device may send a control signal to the IV pump to reduce the rate of infusion to correspond to the rate indicated in the caregiver records, while also sending a notification to a caregiver device and/or to a monitoring computing device to provide an alert regarding the discrepancy.

In addition, after the PC matrix P has been generated and used for identifying any patients having a discrepancy in care for a first treatment subject, such as ventilator compliance, in some cases, the same PC matrix may be used for other treatment subjects. Thus, the PC matrix P may be used for determining patients who may have experienced a discrepancy in care for different patient treatment subjects, and accordingly, different vectors Y, may be quickly processed using the same matrix P of PCs. For instance, the patients who may have experienced a discrepancy in care for IV pumps (vector $Y_2$ in FIG. 4) may be determined by clustering the same PC matrix 500 into five clusters, matching the five clusters to 5 groups using the same method described in FIG. 6, and constructing a confusion matrix similar to FIG. 7A.

Various instructions, processes, and techniques described herein may be considered in the general context of computer-executable instructions, such as program modules stored on computer-readable media, and executed by the processor(s) herein. Generally, program modules include routines, programs, objects, components, data structures, executable code, etc., for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed:

1. A system comprising:
one or more processors; and
one or more non-transitory computer-readable media maintaining executable instructions, which, when executed by the one or more processors, program the one or more processors to perform operations comprising:
receiving sensor data from patient devices, wherein individual patients of a plurality of patients each have a plurality of the patient devices associated therewith;
receiving caregiver records corresponding at least partially to the sensor data;
determining a vector from the caregiver records based on a selected subject;
determining a plurality of clusters from the sensor data;
determining, from the vector, a plurality of groups corresponding to the plurality of clusters;
based on the plurality of clusters and the plurality of groups, determining an indication of a discrepancy in care for a patient of the plurality of patients; and
sending at least one of:
a notification to a caregiver device;
a notification to a monitoring computing device; or
a control signal to control a patient device at a patient location associated with the patient indicated to have a discrepancy in care.

2. The system as recited in claim 1, wherein:
the vector includes at least two of the groups, each group corresponding to a different indicator in the vector; and
a number of the clusters is equal to a number of the groups in the vector.

3. The system as recited in claim 1, the operations further comprising, prior to determining the plurality of clusters, summarizing the received sensor data into a data structure, wherein the received sensor data includes a plurality of waveform data that is summarized into respective values that are representative of the waveform data over a time interval.

4. The system as recited in claim 3, the operations further comprising:
prior to determining the clusters, determining principal components of the data structure;
determining the plurality of clusters from the sensor data by selecting one or more top principal components that correspond to greater than a threshold percentage of variability in the data structure; and
generating the clusters based on the selected principal components.

5. The system as recited in claim 3, wherein:
the data structure includes a number of entries corresponding to a number of patients and a number of time intervals per patient over a time period; and
the vector includes a number of entries corresponding to the number of patients and the number of time intervals per patient over the time period.

6. The system as recited in claim 1, wherein the caregiver records include data related to individual patients manually entered into a caregiver device in at least one of a structured data format or a freeform data format.

7. The system as recited in claim 1, the operations further comprising:
determining a center of each cluster and a center of a group corresponding to a respective cluster;
determining a minimum distance between the center of each cluster and the center of the group corresponding to the cluster;
determining a matrix including indicators from the groups that correspond to the clusters; and
determining patient identifiers from elements of the matrix for identifying the patient indicated to have the discrepancy in care.

8. A method comprising:
receiving, by a processor, sensor data associated with a plurality of patient devices associated with a plurality of patients;
receiving caregiver records corresponding at least partially to the sensor data;
determining at least two groups of indicators from the caregiver records;
determining a plurality of clusters from the sensor data;
based on the plurality of clusters and the at least two groups, determining an indication of a discrepancy in care for a patient of the plurality of patients; and
sending at least a notification based on the indication of the discrepancy.

9. The method as recited in claim 8, further comprising determining a vector based on a selected subject that includes the at least two groups of indicators, each group corresponding to a different indicator in the vector, wherein a number of the clusters is equal to a number of the groups in the vector.

10. The method as recited in claim 9, further comprising, prior to determining the plurality of clusters, summarizing the received sensor data into a data structure, wherein the received sensor data includes a plurality of waveform data that is summarized into respective values that are representative of the waveform data over a time interval.

11. The method as recited in claim 10, further comprising:
prior to determining the clusters, determining principal components of the data structure;
determining the plurality of clusters from the sensor data by selecting one or more top principal components that correspond to greater than a threshold percentage of variability in the data structure; and
generating the clusters based on the selected principal components.

12. The method as recited in claim 10, further comprising:
generating the data structure to include a number of entries corresponding to a number of patients and a number of time intervals per patient over a time period; and
generating the vector to include a number of entries corresponding to the number of patients and the number of time intervals per patient over the time period.

13. The method as recited in claim 8, further comprising:
receiving the caregiver records including data related to individual patients manually entered into a caregiver device in at least one of a structured data format or a freeform data format; and at least one of:
sending the notification to the caregiver device;
sending the notification to a monitoring computing device; or
sending a control signal to control a patient device at a patient location associated with the patient indicated to have a discrepancy in care.

14. The method as recited in claim 8, further comprising:
determining a center of each cluster and a center of a group corresponding to a respective cluster;
determining a minimum distance between the center of each cluster and the center of the group corresponding to the cluster;
determining a matrix including indicators from the groups that correspond to the clusters; and
determining patient identifiers from elements of the matrix for identifying the patient indicated to have the discrepancy in care.

15. A system comprising:
one or more processors; and
one or more non-transitory computer-readable media maintaining executable instructions, which, when executed by the one or more processors, program the one or more processors to:
receive sensor data associated with a plurality of patient devices associated with a plurality of patients;
receive caregiver records corresponding at least partially to the sensor data;
determine at least two groups of indicators from the caregiver records;
determine a plurality of clusters from the sensor data;
based on the plurality of clusters and the at least two groups, determine an indication of a discrepancy in care for a patient of the plurality of patients; and
sending at least a notification based on the indication of the discrepancy.

16. The system as recited in claim 15, wherein the one or more processors are further programmed to:
determine a vector based on a selected subject that includes the at least two groups of indicators, each group corresponding to a different indicator in the vector; and
a number of the clusters is equal to a number of the groups in the vector.

17. The system as recited in claim 16, wherein the one or more processors are further programmed to, prior to determining the plurality of clusters, summarize the received sensor data into a data structure, wherein the received sensor data includes a plurality of waveform data that is summarized into respective values that are representative of the waveform data over a time interval.

18. The system as recited in claim 17, wherein the one or more processors are further programmed to:
- prior to determining the clusters, determine principal components of the data structure;
- determine the plurality of clusters from the sensor data by selecting one or more top principal components that correspond to greater than a threshold percentage of variability in the data structure; and
- generate the clusters based on the selected principal components.

19. The system as recited in claim 17, wherein:
- the data structure includes a number of entries corresponding to a number of patients and a number of time intervals per patient over a time period; and
- the vector includes a number of entries corresponding to the number of patients and the number of time intervals per patient over the time period.

20. The system as recited in claim 15, wherein:
- the caregiver records include data related to individual patients manually entered into a caregiver device in at least one of a structured data format or a freeform data format; and
- the one or more processors are further programmed to at least one of:
  - send the notification to the caregiver device;
  - send the notification to a monitoring computing device; or
  - send a control signal to control a patient device at a patient location associated with the patient indicated to have a discrepancy in care.

* * * * *